United States Patent [19]

Hammond

[11] Patent Number: 4,579,736

[45] Date of Patent: Apr. 1, 1986

[54] INHIBITION OF PLAQUE-FORMING BACTERIA

[75] Inventor: Benjamin F. Hammond, Philadelphia, Pa.

[73] Assignees: Colgate-Palmolive Co., New York, N.Y.; University of Pennsylvania, Philadelphia, Pa.

[21] Appl. No.: 589,198

[22] Filed: Mar. 13, 1984

[51] Int. Cl.$^4$ ............................................. A61K 35/78
[52] U.S. Cl. .................................................. 424/195.1
[58] Field of Search ............................. 424/195, 195.1

[56] References Cited

U.S. PATENT DOCUMENTS 4,133,875  1/1979  Hillman ................................. 424/93
4,458,014  7/1984  Ebersole ................................ 435/7

Primary Examiner—Albert T. Meyers
Assistant Examiner—John W. Rollins, Jr.

[57] ABSTRACT

Water-soluble extract of sonically induced disintegration of *Actinobacillus actinomycetemcomitans* causes inhibition of growth and metabolism of bacteria associated with plaque formation. The water-soluble extract contains factors which are specifically inhibitory to these organisms.

4 Claims, No Drawings

INHIBITION OF PLAQUE-FORMING BACTERIA

Many adult individuals have a tendency to form plaque which could lead to periodontitis. The latter generally occurs in adults. However, there is a condition, juvenile periodontitis, which does effect a small number of juveniles, particularly females, in which localized periodontitis occurs, albeit without significant supragingival plaque formation.

A reciprocal relationship has been observed between *Actinobacillus actinomycetemcomitans* (*A. a.*) which is present in the oral cavities in juveniles, including those having localized periodontitis and bacteria associated with formation of plaque, such as *Streptococcus sanguis* (*S. sang.*) and *Actinomyces viscosus* (*A. vis.*)

It is an advantage of this invention that inhibition of growth and metabolism of bacteria-associated with plaque formation is attained.

It is a further advantage of this invention that a procedure for producing factor from *A. a.* which is specifically inhibitory to growth and metabolism of plaque-forming bacterial, and the factor itself, is provided.

Additional advantages of the invention will be apparent from consideration of the following specification.

*A. a.* strains and clinical isolates thereof are readily available and have been widely grown. Deposited ATCC strains among these are ATCC 29522, ATCC 29523 and ATCC 29524; $Y_4$ and 627 are other very desirable strains.

In the practice of the invention, *A. a.* is exposed to sonic energy to break down its cell walls and disintegrate it into water-soluble and water-insoluble sonic extracts or portions, the extracts or portions are separated by centrifugation and the soluble portion is harvested by decanting it from the centrifuged insoluble portion; crude factors of the soluble portion having a molecular weight of at least about 12,000 are then retained by dialysis and the crude factors are concentrated by lyophilization and placed in contact with plaque-forming bacterial, thereby inhibiting said plaque-forming bacterial from growing or metabolizing.

In accordance with a further aspect of the invention factors present in the water-soluble extract are separated wherein the lyophilized crude factors are spread apart over an electric field by isoelectric focusing into factors identifiable at isoelectric pH values over a pH range of at least about 5 to 8 which factors are removed from the isoelectric focusing gel by elution with distilled water to obtain factor identified at isoelectric pH of at least one of pH 5.1 and pH 6.8 and said factor is placed in contact with plaque-forming bacterial, thereby inhibiting said plaque-forming bacterial from growing and metabolizing.

In the procedure, ultrasound is typically employed as the sonic energy to disintegrate *A. a.*, centrifugation is typically conducted at about 16,000×gravity, harvesting by decanting. Dialysis is conducted in a conventional manner as is lyophilization (freeze drying).

In the aspect of the invention wherein the factors are separated from the crude extract, isoelectric focusing is employed to separate the crude factors by electric charge and spread them over an electric field according to factors identifiable by isoelectric pH, the factors being proteinaceous in nature. In the isoelectric focusing procedure, the lyophilized crude factors are suspended in about 0.5% of glycine (a buffer), and then analyzed in gels. LKB Ultradex Ampholyne gels having desirable isoelectric points were used. Isoelectric focusing proceeds under standard conditions therefor. When proteins identifiable by isoelectric pH over a pH range of at least 5–8 are seen by means of protein dyes, they can be readily removed by elution with distilled water into factors having isoelectric pH values over the broad pH range, such as about 5 to about 8.

The effectiveness of the lyophilized water-soluble sonic extract and of the several factors in inhibition of plaque-forming bacteria, such as *S. sang.* and/or *A. visc.* can be determined by bacterial growth inhibition and inhibition of metabolism techniques. It is observed that the sonic extract is effective and that of the separated factors identified by isoelectric pH, values over a broad range, the factors identified at isoelectric pH of 5.1 and of 6.8 inhibit growth and metabolism of *S. sang.* or *A. visc.* when contacted therewith.

The actinobacillus inhibitory factor (AIF) nature of the factors identified at isoelectric pH of 5.1 and of 6.8 as well as of the water-soluble sonic extract is confirmed by growth inhibition diffusion and turbidometric assay techniques with plaque-forming bacterial. Also, each of the pH 5.1 and 6.8 AIFs reduces the ability of *S. sang.* and *A. visc.* to metabolize glucose. The sonic extract and each of the pH 5.1 and 6.8 AIFs provide substantial inhibition of growth of plaque-forming bacterial whereas with factors identified at other isoelectric pH values and with control in which no additive is employed, growth of plaque-forming bacterial is substantial and there is little inhibition of metabolism.

The lyophilized crude factors can be further characterized by eluting the crude factor after lyophilization by gel filtration, for instance, using Sephadex G-100 (0.01M phosphate buffer and 0.0015M sodium chloride; pH 7.5), to provide factors having a molecular weight of about 40,000–68,000. When these factors are subjected to isoelectric focusing, it is determined that the AIFs identified as having isoelectric pH of 5.1 and 6.8 are among the factors having a molecular weight in the range of 40,000–68.000. Thus, this gel filtration elution step prior to isoelectric focusing may be incorporated into the procedure of the invention.

The AIF and AIF activity in the sonic extract are further characterized as being proteinaceous, inhibited by proteolytic enzyme, e.g. Pronase and trypsin, sensitive to heat and inhibited by antibodies prepared against whole cells of *A. a.* The AIFs undergo 50% reduction in activity upon exposure to 56° C. for 30 minutes.

The following specific examples are further illustrative of the nature of the present invention, but is is understood that the invention is not limited thereto.

EXAMPLE 1

*A. a.* strain $Y_4$ is grown in 100 ml of Brain Heart Infusion Broth (BHI) for 18 hours and then disintegrated by exposure to ultrasound sonic energy into water-soluble and water-insoluble extracts. The extracts are separated by centrifugation at 16,000×gravity and the mixed factors in the water-soluble extract are harvested by decanting.

Conventional dialysis is employed to remove low molecular weight factors while retaining factors having a molecular weight of at least about 12,000. The retained factors are lyophilized by freeze drying at about −52° C. The foregoing steps are in accordance with the procedure described in Tsai et al, "Infection and Immunity", Vol. 25, pages 427–439, 1979).

The lyophilized sonic extract is tested for ability to inhibit *S. sang.* as follows:

Inhibition of growth assay—Well technique

Shallow wells cut into the agar surface of lawns showing confluent growth of the test organism *S. sang.* and the wells subsequently filled with the lyophilized sonic extract. Plates are incubated for 24 hours at 37° C. and then examined to see if zones of inhibition of growth occur around wells. Control cells contain saline. The sonic extract is effective to inhibit growth.

In a modification of the foregoing procedure, after lyophilization the concentrated factors are subjected to gel filtration by dissolving them in Sephadex G-100 molecular sieve with buffer containing 0.01M phosphate buffer and 0.0015M sodium chloride at pH 7.5, thereby obtaining factors having a molecular weight about 40,000-68,000. The concentrated factors inhibit growth of *S. sang.*

As further modifications strain 627, ATCC 29522, ATCC 29523 and AATC 29524 are each used in place of strain Y$_4$, each in mixture with each other and/or with strain Y$_4$.

EXAMPLE 2

Each of the lyophilized sonic extracts and the 40,000-68,000 molecular weight concentrates produced as described in Example 1 are subjected to isoelectric focusing for 18 hours at 9° C. with a constant power of about 9 watts, a maximum voltage of about 1,400 volts and a maximum amperage of about 18 milliamps, with the factors being in LKB Ultradex gel. By virtue of this procedure, factors identifiable by isoelectric pH over a pH range including pH 5-8 are seen by means of protein dyes. The identified factors are removed from the iseoelectric focusing gel electric field by elution with distilled water.

The separated factors are tested for ability to inhibit growth *S. sang.* in the well technique, previously described. The factors tested are those identified with pH units from 5.0 to 8.0 in increments about 0.1-0.3 pH units.

The factors identified by isoelectric pH of 5.1 and of 6.8 are successful as AIFs. These factors remain 50% active when heated for 1 hour at 56° C.

The AIF effectiveness of the factors identified by isoelectric pH of 5.1 and of 6.8 and of the lyophilized sonic extracts are confirmed in the following tests:

Inhibition of growth assay—Turbidometric assay technique

This assay is based on the inhibition of cell growth in a broth medium as determined turbidometrically in a spectrophotometer. *S. sang.* is washed twice in sterile saline. The washed cells are then suspended in enough sterile saline to give an optical density of 25 in the Klett Summerson colorimeter 660 filter. Enough of each of the lyophilized sonic extracts in one case and pH 5.1 and/or 6.8 AIFs in others are added to the washed, standardized cell suspensions to give final concentrations of 75 microgram/ml. The cell suspensions are allowed to incubate with each of the sonic extracts with the AIF preparations for one hour at 37° C. After exposure, the cells are centrifuged down (16,000×gravity), washed in saline as before to eliminate residual sonic extract and AIFs and then placed in fresh sterile tubes of BHI broth (10 ml). The initial turbidity of the inoculated BHI tubes is less than 5 units on the Klett (660 filter). The increase in turbidity is monitored at various intervals in the Klett but the tubes are incubated at 37° C. The differences in turbidity of the sonic extract exposed cells and of the AIF-exposed cells were measured against the turbidities of two control tubes. Control #1 contains *S. sang.* cells in BHI (10 ml); control #2 contains *S. sang.* cells previously exposed to heat inactivated factors (56° C. for 1 hour); (10 ml). Activity is expressed as percent of the control *S. sang.* cell turbidity (control #2). Caution is taken to ensure proper homogenization of the extract to ensure uniform turbidity. Standardization of sonic extract and of the AIFs is accomplished by expressing activity per mg of cell protein as determined by the Lowry procedure (J. Biol. Chem., Vol. 193, pages 265–275, 1951).

Each of the sonic extract and the pH 5.1 and 6.8 AIFs provide substantial inhibition of growth of *S. sang.*, while with the controls, growth of *S. sang.* increases in a logarithmic manner over a 15-hour period.

Inhibition of metabolism technique

This technique is based on the ability of the AIFs to interfere with the utilization of glucose. In this assay washed, resting *S. sang.* cells metabolize glucose (100 micrograms/ml) in 0.01M phosphate buffered saline (0.01M $PO_4$, 0.0015M NaCl, pH 7.5) to which the AIFs are separately added (final concentration of 75 microgram/ml). The ability of AIF-treated cells to metabolize glucose is determined by monitoring the amount of glucose remaining at various intervals during a 60-minute time period. Control *S. sang.* cells in the absence of AIF of *S. sang.* cells+heat inactivated factors are used to determine 100% baseline value for glucose utilization. The results taken initially (100% in all cases) and after 30 and 60 minutes are a linear function. The *S. sang.* control and the *S. sang.* control with heat inactivated factors effect no inhibition of metabolism of glucose after 60 minutes while the sonic extracts and the pH 5.1 and 6.8 AIFs effect about 60% inhibition of glucose metabolism.

Similar inhibition of bacteria growth and metabolism is observed when *A. visc.* replaces *S. sang.*

By further tests on other crevicular bacteria, particularly Capnocytophaga spp., *Fusobacterium nucleatum*, *Streptococcus mutans* and Veillonella spp., it is determined that the AIF on *S. sang.* and *A. visc.* does not apply to these other bacteria.

It will be apparent to one skilled in the art that various modifications in the foregoing examples may be made thereto.

I claim:

1. The process of forming an inhibitor of growth and metabolism of the plaque-forming bacteria *Streptococcus sanguis* and *Actinomyces viscosus* comprising exposing *Actinobacillus actinomycetemcomitans* to sonic energy to break down its cell walls and disintegrate it into water-soluble and water-insoluble portions, separating the portions by centrifugation at about 16000×gravity and harvesting the soluble portion by decanting, dialyzing the soluble portion to retain crude factors of the soluble portion having a molecular weight of at least about 12,000, and concentrating the crude factors of molecular weight of at least about 12,000 by freeze drying lyophilization.

2. The process claimed in claim 1 wherein said lyophilized crude factors are suspended in about 0.5% by weight of glycine buffer and spread apart over an electric field in an isoelectric focussing gel into factors identifiable at isoelectric pH values over a pH range of at least about 5 to 8 and removing said factors from said isoelectric focussing gel by elution with distilled water to obtain factors at isoelectric pH of at least one of pH 5.1 and pH 6.8.

3. The process claimed in claim 2 wherein factors having isoelectric pH values identified both at pH 5.1 and pH 6.8 are separated by elution.

4. The process claimed in claim 1 wherein after lyophilization the concentrated crude factors of molecular weight of at least about 12,000 are subjected to gel filtration by dissolving them in Sephadex G-100 molecular sieve with buffer containing 0.01M phosphate buffer and 0.0015M NaCl at pH 7.5 to thereby obtain factors having a molecular weight of about 40,000–68,000.

* * * * *